United States Patent
Hori

(10) Patent No.: US 10,617,886 B2
(45) Date of Patent: Apr. 14, 2020

(54) ACCELERATOR AND PARTICLE THERAPY SYSTEM

(71) Applicant: Hitachi, Ltd., Tokyo (JP)

(72) Inventor: Chishin Hori, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/341,065

(22) PCT Filed: Nov. 1, 2017

(86) PCT No.: PCT/JP2017/039483
§ 371 (c)(1),
(2) Date: Apr. 11, 2019

(87) PCT Pub. No.: WO2018/116647
PCT Pub. Date: Jun. 28, 2018

(65) Prior Publication Data
US 2019/0232085 A1    Aug. 1, 2019

(30) Foreign Application Priority Data
Dec. 22, 2016  (JP) ................. 2016-248587

(51) Int. Cl.
*A61N 5/10* (2006.01)
*H05H 13/00* (2006.01)
*H05H 13/08* (2006.01)

(52) U.S. Cl.
CPC ......... *A61N 5/1001* (2013.01); *H05H 13/005* (2013.01); *A61N 2005/1019* (2013.01);
(Continued)

(58) Field of Classification Search
CPC .......... A61N 5/1001; A61N 2005/1087; A61N 2005/1019; H05H 13/005; H05H 2277/11; H05H 13/08
(Continued)

(56) References Cited

U.S. PATENT DOCUMENTS

| 10,117,320 B2 * | 10/2018 | Aoki ................. H05H 7/08 |
| 2008/0093567 A1 * | 4/2008 | Gall ................. A61N 5/1081 250/493.1 |

(Continued)

FOREIGN PATENT DOCUMENTS

| JP | 2009-524200 A | 6/2009 |
| JP | 2013-543248 A | 11/2013 |
| WO | 2016/092621 A1 | 6/2016 |

OTHER PUBLICATIONS

International Search Report of PCT/JP2017/039483 dated Jan. 16, 2018.

*Primary Examiner* — Don P Le
(74) *Attorney, Agent, or Firm* — Mattingly & Malur, PC

(57) ABSTRACT

To provide an accelerator that easily provides a space for placing equipment incorporated into an accelerator magnet, and that has a dense region with small turn separations of beams and a sparse region with large turn separations of the beams in different positions in the beam orbit direction. A pair of magnetic poles (8, 9) has a depression structure of a plurality of depression and projection structures, in a position intersecting with a vertical plane (3). A boundary surface (41, 44, 45, 48) between the depression structure (21, 23) placed in a position intersecting with the vertical plane (3) and a projection structure (31, 32, 33, 34) adjacent to the depression structure has unanimously either a projection shape or a depression shape with respect to the vertical plane (3).

4 Claims, 8 Drawing Sheets

(52) U.S. Cl.
CPC ...... *A61N 2005/1087* (2013.01); *H05H 13/08* (2013.01); *H05H 2277/11* (2013.01)

(58) Field of Classification Search
USPC .......................................................... 315/505
See application file for complete search history.

(56) References Cited

U.S. PATENT DOCUMENTS

| | | |
|---|---|---|
| 2011/0193666 A1 | 8/2011 | Antaya et al. |
| 2012/0126726 A1 | 5/2012 | Antaya |
| 2016/0353562 A1* | 12/2016 | Antaya .................... H01F 6/06 |

* cited by examiner

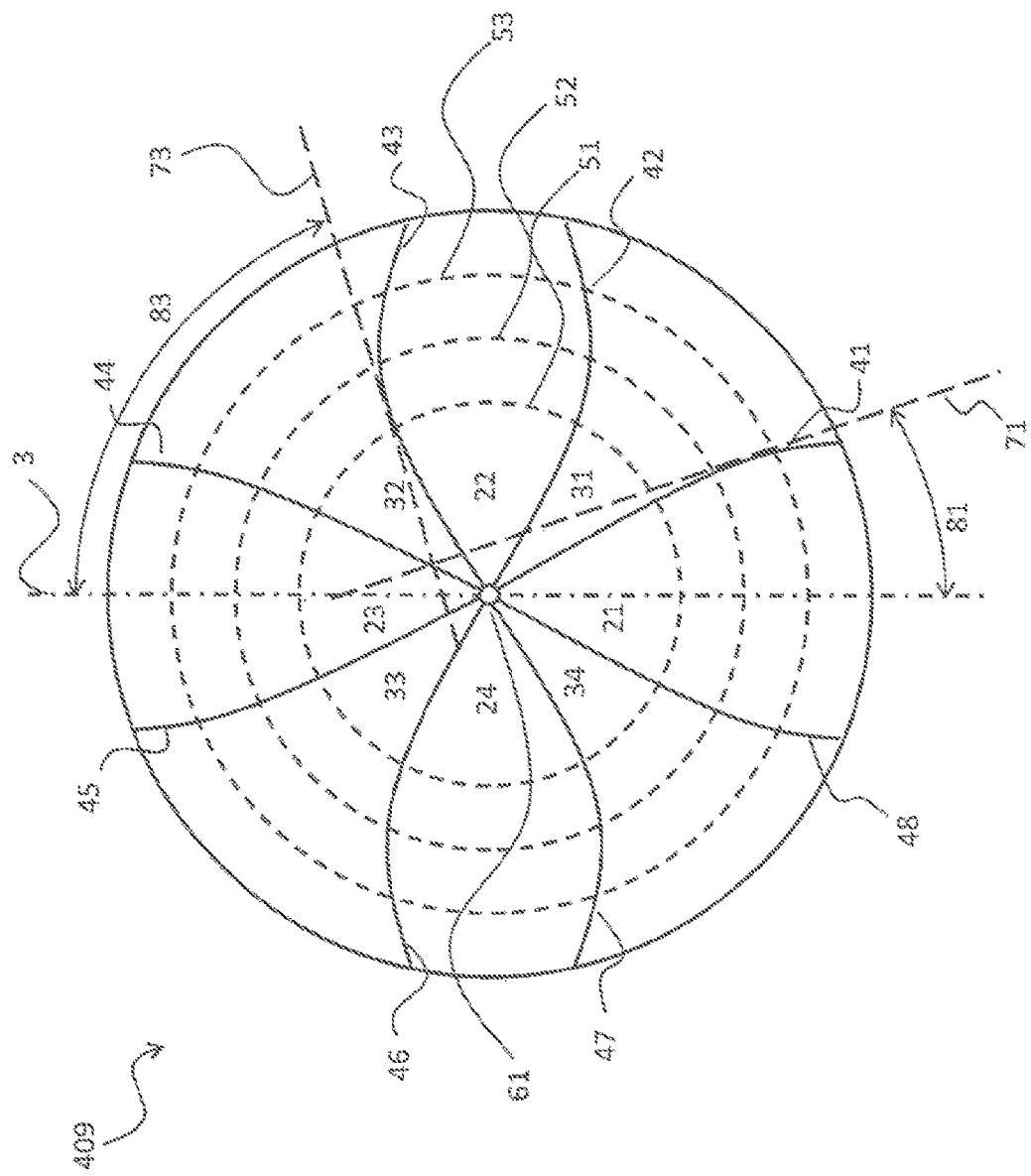

ACCELERATOR AND PARTICLE THERAPY SYSTEM

TECHNICAL FIELD

This invention relates to an accelerator and a particle therapy system with the same.

BACKGROUND ART

In Background Art of the present invention, there is a technology disclosed in Patent Literature 1. Patent Literature 1 proposes a cyclotron accelerator that emits different energy beams with efficiency. In the accelerator disclosed in Patent Literature 1, the positional relationship between different energy beam orbits is not approximately concentric, and the centers of the beam orbits move linearly in one direction from low energy to high energy. Because of this, a dense region with a small distance between adjacent beam orbits (turn separation) and a sparse region with a large distance in reverse are located in different positions in the beam orbit direction. Specifically, because of a region in which a turn separation of high-energy beams is larger than that in approximately concentric beam orbits, a selective extraction of beams can be facilitated.

CITATION LIST

Patent Literature

Patent Literature 1: WO2016/092621

SUMMARY OF INVENTION

Technical Problem

Patent Literature 1 discloses a magnetic field distribution for achieving beam orbit with the dense region and the sparse region (FIG. 10 of Patent Literature 1) and a magnetic pole shape for achieving the magnetic field distribution (FIG. 30 of Patent Literature 1). The magnetic field distribution disclosed in Patent Literature 1 smoothly changes, like a trigonometric function, between a maximum value and a minimum value along the beam orbit direction. In order to achieve the smooth magnetic field change, the upper and lower magnetic pole surfaces of the magnet apparatus, both facing the beam orbit plane, have projections and depressions smoothly formed thereon along the beam orbit direction, as a natural result.

A region located between a pair of upper and lower projections is referred to as a hill region, and similarly a region located between a pair of upper and lower depressions is referred to as a valley region. In general, in the cyclotrons, an acceleration cavity is placed in the valley region and a trim coil for fine adjustment of a main magnetic field, and/or the like is placed in the hill region. If the magnetic pole surface smoothly changes in shape like a trigonometric function, this gives rise to complication of placement and shape of equipment incorporated into such an accelerator magnet.

Therefore, a technical problem of the present invention is to provide an accelerator that easily provides a space for placing equipment incorporated into an accelerator magnet, and that has a dense region with small turn separations of beams and a sparse region with large turn separations of the beams in different positions in the beam orbit direction. And also, a technical problem of the present invention is to provide a particle therapy system including the accelerator.

Solution to Problem

To solve the problems, an aspect of the present invention provides an accelerator that has a pair of cores formed in disk shape, a pair of magnetic poles fixed to circular surfaces of the cores, a pair of coils placed around the magnetic poles. The accelerator has a space between the pair of magnetic poles for circulating and accelerating ion beam. The pair of magnetic poles has a plurality of depression and projection structures arranged along an orbit of the ion beam circulating. The magnetic poles are plane-symmetric with respect to an orbit plane created by the orbit of the ion beam circulating as well as plane-symmetric with respect to one of vertical planes perpendicular to the orbit plane. The pair of magnetic poles has a depression structure of the plurality of depression and projection structures, in a position intersecting with the vertical plane, and a boundary surface between the depression structure placed in a position intersecting with the vertical plane and a projection structure adjacent to the depression structure has unanimously either a projection shape or a depression shape with respect to the vertical plane.

Advantageous Effects of Invention

According to the present invention, because the boundary surface between the depression and the projection varies approximately vertically along the beam orbit direction, this facilitates providing a space for placing equipment incorporated into an accelerator magnet. Because the depressions containing the vertical symmetry plane differ in area, a dense region with small turn separations of beams and a sparse region with large turn separations of the beams occur.

BRIEF DESCRIPTION OF DRAWINGS

FIG. 8 is a plan view of a magnetic pole surface with approximately concentric beam orbits and different spacings between magnetic poles in each set of projections/depressions.

DESCRIPTION OF EMBODIMENTS

Embodiments for practicing the present invention will be now described with reference to each figure.

First Embodiment

First, the structure of a magnet apparatus 1 will be described with reference to FIG. 1 to FIG. 4.

Figure 1:
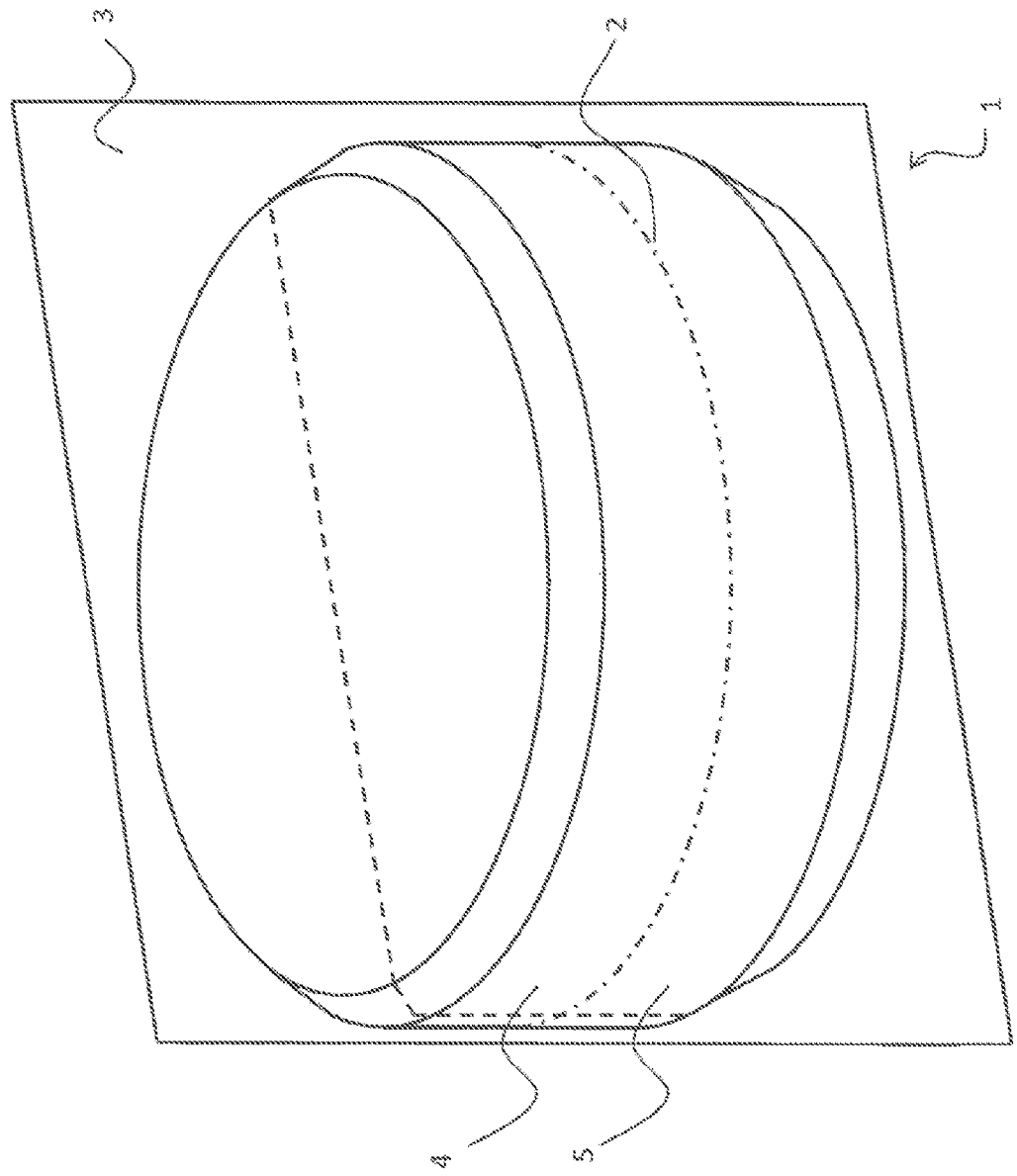
FIG. 1 is a perspective view of an accelerator in accordance with a first embodiment.

FIG. 1 is a perspective view of a magnet apparatus 1. The magnet apparatus 1 has, as main components, an upper core 4 and a lower core 5 which form an approximate disk shape when viewed in the vertical direction as illustrated in FIG. 1. The upper core 4 and the lower core 5 have approximately vertically symmetric shapes with respect to a horizontal symmetry plane 2. The horizontal symmetry plane 2 is a plane which passes through an approximate vertical center of the magnet apparatus 1 and is parallel to orbit created by accelerating ions. The upper core 4 and the lower core 5 have plane symmetric shapes with respect to a vertical symmetry plane 3. The vertical symmetry plane 3 is a plane perpendicular to the horizontal symmetry plane 2 and also passing through an approximate center of the magnet apparatus 1 with respect to the horizontal symmetry plane 2. Incidentally, in FIG. 1, intersection of the horizontal symmetry plane 2 with the magnet apparatus 1 is shown by a dash-dot line, and intersection of the vertical symmetry plane 3 with the magnet apparatus 1 is shown by a broken line.

Figure 2:
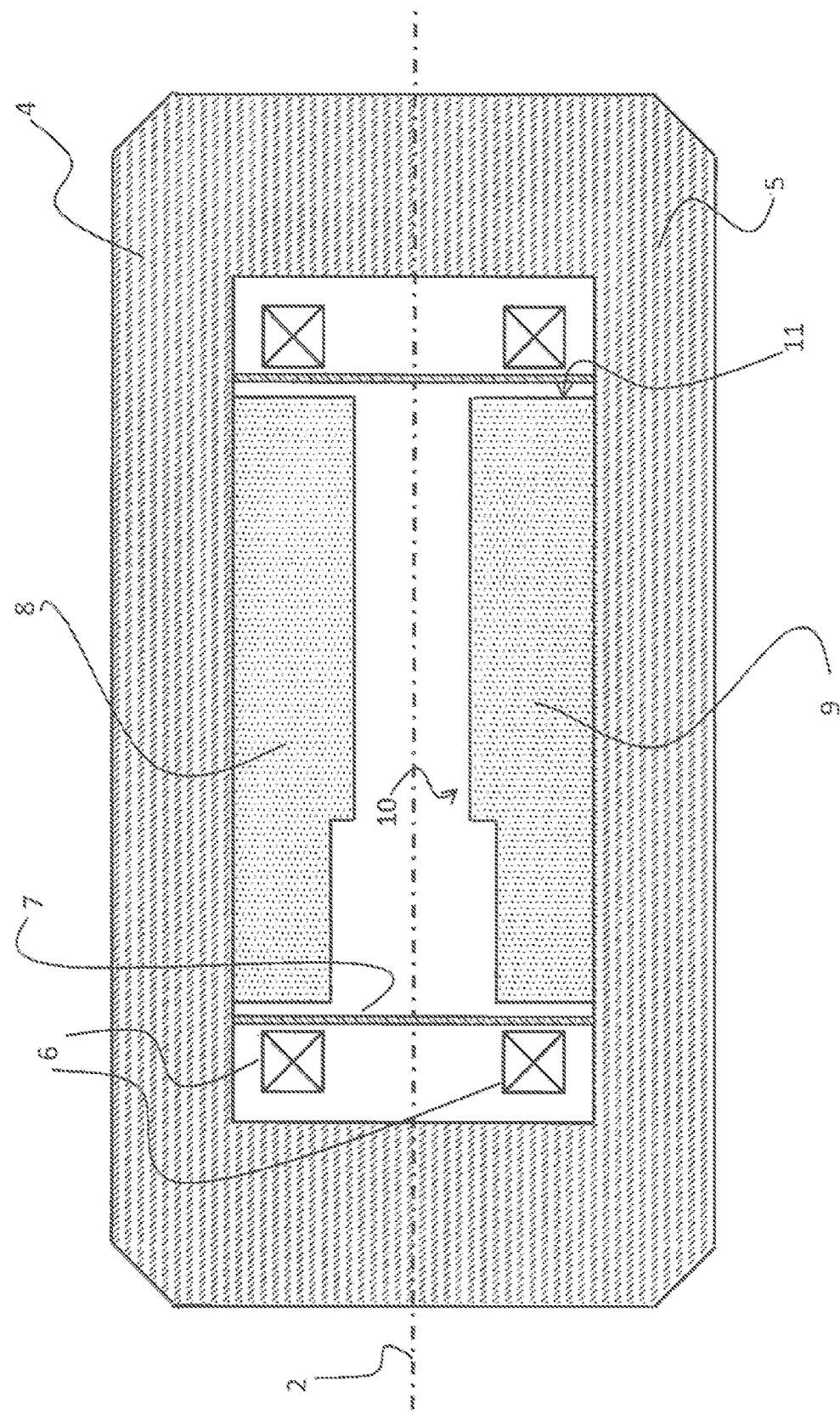
FIG. 2 is a sectional view of the accelerator in accordance with the first embodiment.

FIG. 2 is a sectional view of the magnet apparatus 1 along the vertical symmetry plane 3. Coils 6 are placed plane-symmetrically with respect to the horizontal symmetry plane 2 within a space enclosed with the upper core 4 and the lower core 5, and likewise an upper magnetic pole 8 and a lower magnetic pole 9 are placed plane-symmetrically with respect to the horizontal symmetry plane 2. In the positional relationship between the coil 6 and each magnetic pole, the coil 6 is placed around each magnetic pole as illustrated in FIG. 2. It is noted that each of the coils 6 may be either superconducting coil or normal conducting coil. A vacuum vessel 7 is also installed in the space enclosed with the upper core 4 and the lower core 5. The upper magnetic pole 8 and the lower magnetic pole 9 are placed within the vacuum vessel 7, and are coupled respectively to the upper core 4 and the lower core 5. Because the magnetic apparatus 1 has a vertical symmetric structure with respect to the horizontal symmetry plane 2, a magnetic pole surface 10 of the lower magnetic pole 9 will be described below in detail.

Figure 3:
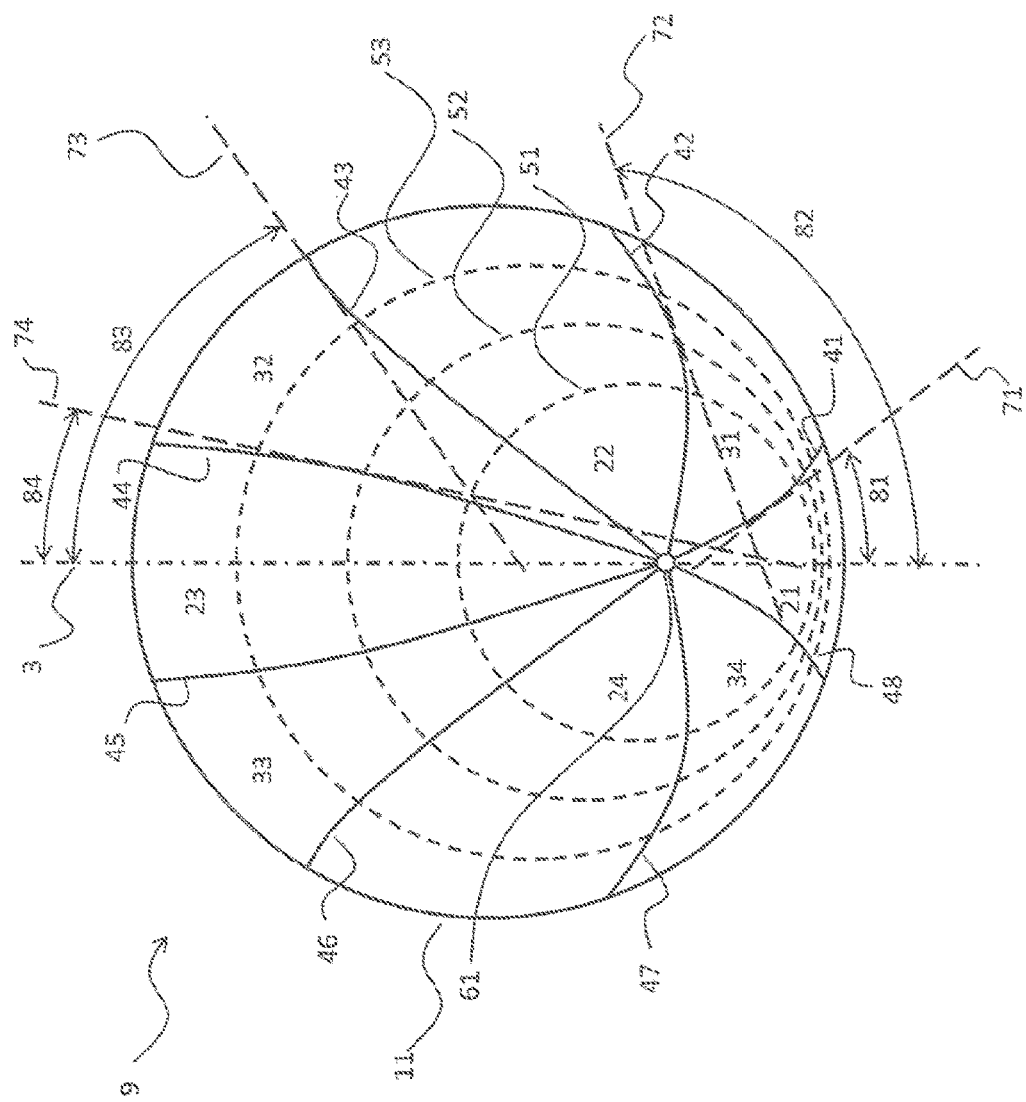
FIG. 3 is a plan view of a magnetic pole of the accelerator in accordance with the first embodiment.

FIG. 3 is a plan view of the magnetic pole surface 10 when viewed from the horizontal symmetry plane 2. On the magnetic pole surface 10, depressions 21, 22, 23, 24 and projections 31, 32, 33, 34, which are shown by solid lines, are alternately placed across the orbit direction of beam orbits 51, 52, 53, and are plane-symmetric with respect to the vertical symmetry plane 3. It is noted that, in the structure of the magnet apparatus 1 in accordance with the embodiment as seen from the figure, the upper magnetic pole 8 and the lower magnetic pole 9 have a plurality of depression and projection structures arranged along the orbit of ion beams moving round and round, and also the upper magnetic pole 8 and the lower magnetic pole 9 are plane-symmetric with respect to the orbit plane created by the beam orbit as well as plane-symmetric with respect to a single vertical symmetry plane 3 perpendicular to the orbit plane.

Each of the depressions and projections has an approximately fan shape. And, in a position on which the tops of the fan shapes of the respective depressions and projections are concentrated, a void 61 exists for placing an ion injector. It is noted that the void 61 may be interpreted as an ion injection point on the magnetic pole surface 10.

Here, a feature of the embodiment is shapes of the depression and the projection when viewed from the horizontal symmetry plane 2, and thus a shape presented by the boundary surface between the depression and the projection is described in detail. It is noted that, in an actual apparatus, in the conditions when viewed from the horizontal symmetry plane 2, it is inevitable that an intermediate region is formed between the depression and the projection, but the following description is based on the assumption that there is no intermediate region between the depression and the projection for the purpose of clarity.

The shapes of the depression 21 and the projection 31 are described first. For describing the shapes, in FIG. 3, where the boundary between the two is a boundary surface 41 and a tangent 71 is drawn to the boundary surface 41, an angle formed between the tangent 71 and the vertical symmetry plane 3 is assumed as an angle 81. In the embodiment, the angle 81 weakly increases as a contact point between the tangent 71 and the boundary surface 41 is moved from proximity to the void 61 toward an outer periphery 11, and the boundary surface 41 draws a curve of downward projection when viewed from the vertical symmetry plane 3. Likewise, for the projection 31 and the depression 22, the boundary between the projection 31 and the depression 22 is a boundary surface 42, and a tangent 72 to the boundary surface 42 forms an angle 82 with the vertical symmetry plane 3. The boundary between the projection 32 and the depression 22 is a boundary surface 43, and a tangent 73 to the boundary surface 43 forms an angle 83 with the vertical symmetry plane 3. The angle 82 and the angle 83 monotonically increase as the contact point is moved from the void 61 toward the outer periphery 11. The boundary surface 42 and the boundary surface 43 exhibit a projection shape protruding with respect to the vertical symmetry plane 3. On the other hand, a tangent 74 to the boundary surface 44 between the depression 23 and the projection 32 forms an angle 84 with the vertical symmetry plane 3. The angle 84 weakly decreases as the contact point is moved from the void 61 toward the outer periphery 11. The boundary surface 44 exhibits a projection shape protruding from the vertical symmetry plane 3. The depression 21 and the depression 23, containing the vertical symmetry plane 3, are different in area. In the first embodiment, the area of the depression 21 is smaller and the area of the depression 23 is larger.

The depression and projection structure described above may be described as follows. Specifically, a pair of magnetic poles, which are placed on the opposite sides of the orbit plane to each other, has a depression structure (the depression 21 and the depression 23) of the plurality of depression and projection structures in a position intersection with the vertical symmetry plane 3. The boundary surface (41, 44, 45, 48) between the depression structure and a projection structure (projection 31, 32, 33, 34) adjacent to the depression structure unanimously takes a projection shape or a depression shape with respect to the vertical symmetry plane 3.

Alternatively, the plurality of depression and projection structures may each also be referred to as a fan-shaped region having a top at the void 61 (injection point) and an arc along the outer edge of each core, and therefore may be described as follows. Specifically, for the depression 21, 23 intersecting the vertical symmetry plane 3 in the plurality of depression and projection structures, an acute angle 81 is formed with the vertical symmetry plane 3 by a tangent (only the tangent 71 is illustrated) to the boundary surface 41, 48 between a depression structure (depression 21) with a short distance from the injection point (void 61) to the arc, and the projection structure (projection 31, 34) adjacent to the depression structure, and the acute angle 81 monotonically increases as the contact point between the tangent 71 and the boundary surface 41 is moved from the void 61 toward the outer edge of the core.

On the other hand, an acute angle 84 is formed with the vertical symmetry plane 3 by a tangent (only the tangent 74 is illustrated) to the boundary surface 44, 45 between a depression structure (depression 23) with a long distance from the injection point (void 61) to the arc, and the projection structure (projection 32, 33) adjacent to the depression structure, and the acute angle 84 monotonically decreases as the contact point between the tangent 74 and the boundary surface 44 is moved from the void 61 toward the outer edge of the core.

Figure 4:
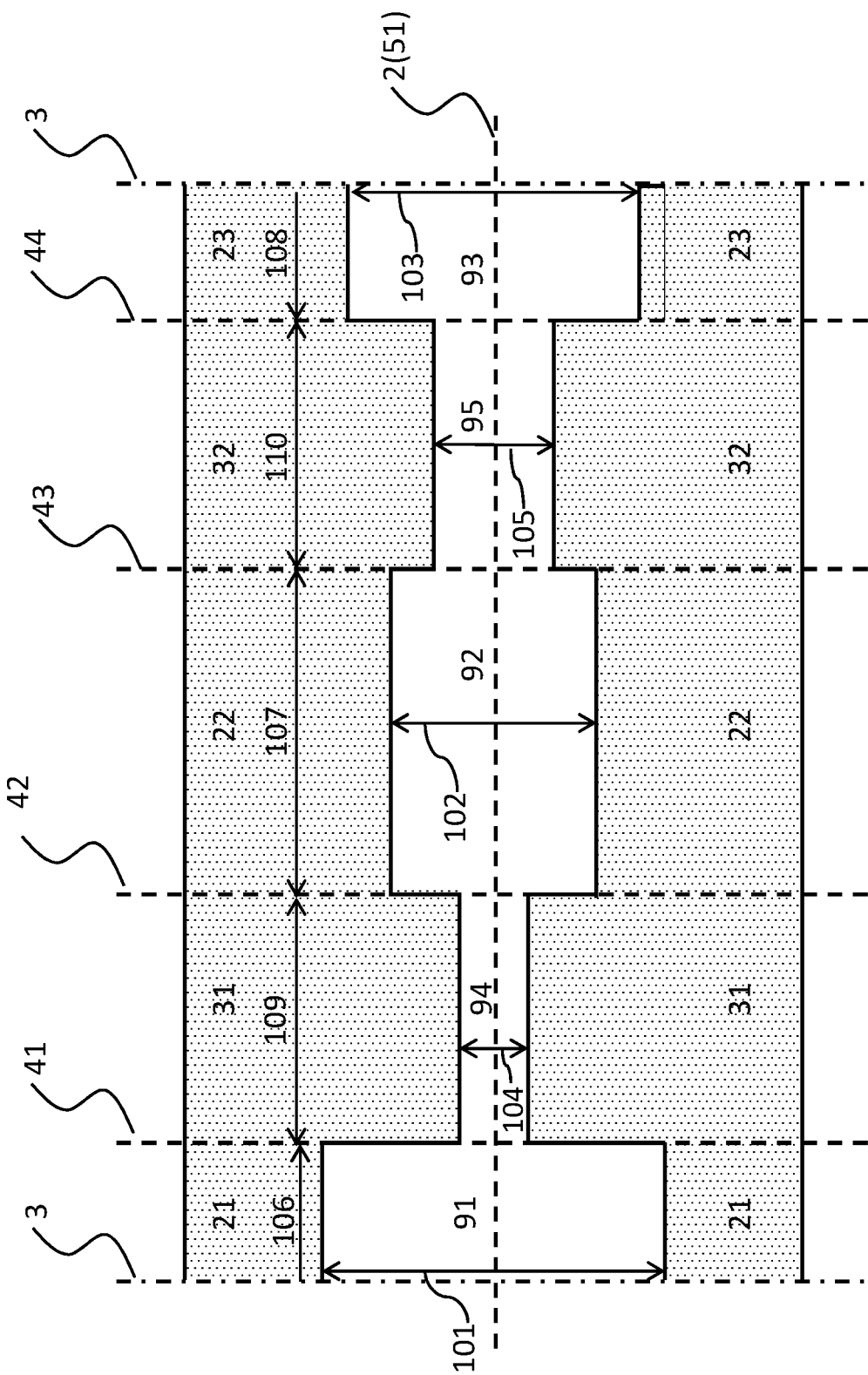
FIG. 4 is a sectional view of the magnetic pole of the accelerator in accordance with the first embodiment.

FIG. 4 is a sectional view of the upper magnetic pole 8 and the lower magnetic pole 9 along the beam orbit 51 shown in FIG. 3. A valley region 91 located between the upper and lower depressions 21, a hill region 94 located between the upper and lower projections 31, a valley region 92 located between the upper and lower depressions 22, a hill region 95 located between the upper and lower projections 32, and a valley region 93 located between the upper and lower depressions 23 are arranged along the beam orbit 51. The boundary surfaces 41, 42, 43, 44 are approximately perpendicular to the horizontal symmetry plane 2. A magnetic pole spacing 101 in the valley region 91, a magnetic pole spacing 102 in the valley region 92 and a magnetic pole spacing 103 in the valley region 93 are different in design value, and similarly a magnetic pole spacing 104 in the hill region 94 and a magnetic pole spacing 105 in the hill region 95 are different in design value.

Next, for comparative description of effects of the above-described structure, a conventional sector cyclotron magnet apparatus 201 will be described with reference to FIG. 5 to FIG. 7. Incidentally, the reference signs used to describe the structure in the magnet apparatus 1 are correspondingly used for reference signs in the figures used to describe the magnet apparatus 201.

Figure 5:
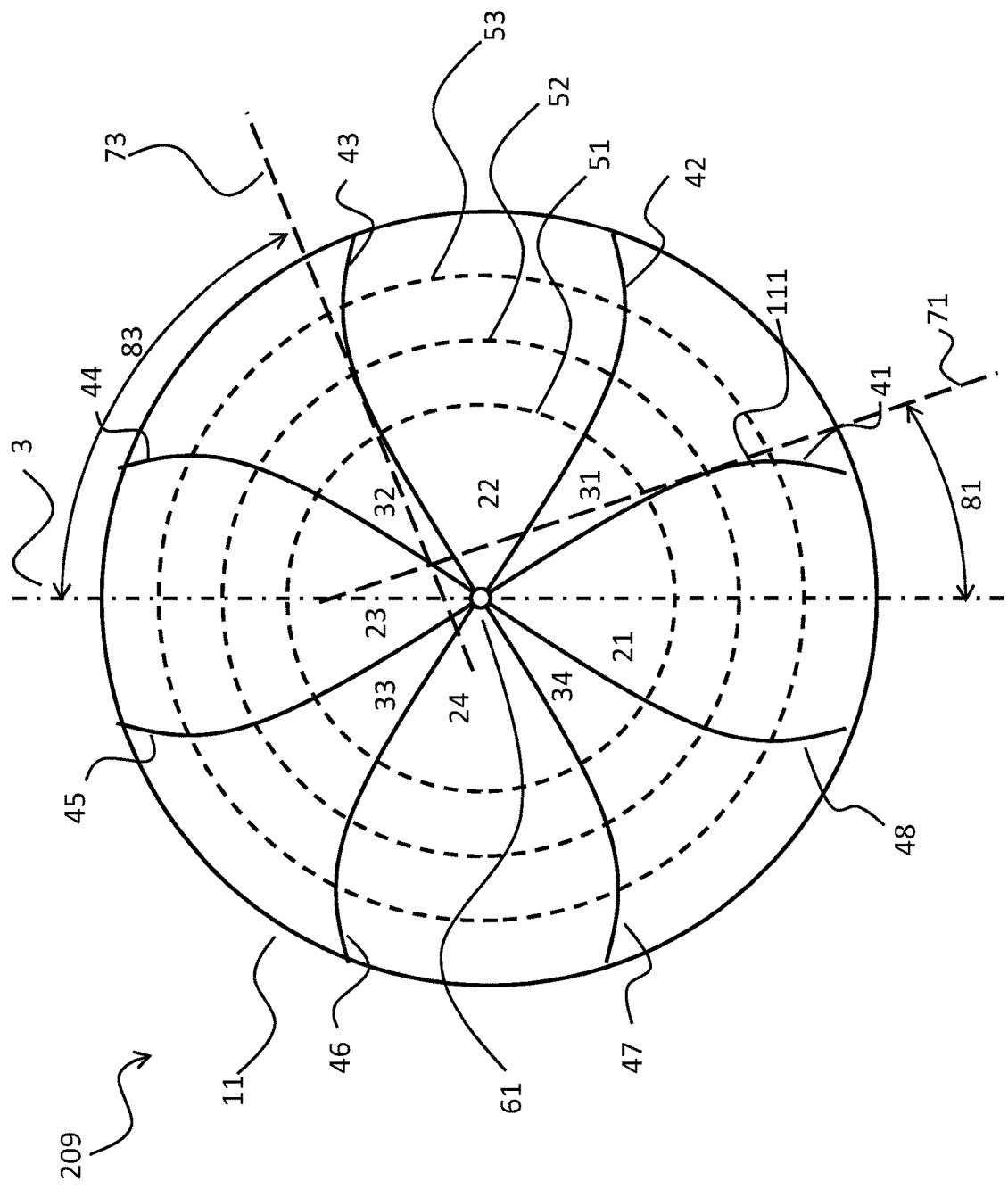
FIG. 5 is a plan view of a magnetic pole surface of a sector cyclotron accelerator.

FIG. 5 is a plan view of a magnetic pole 209 of the magnet apparatus 201. In the sector cyclotron, a plurality of depressions and a plurality of projections are each designed as approximately the same shape. Also, the angle 81 monotonically decreases in the direction from the void 61 toward the outer periphery 11, and the boundary surface 41 is an upward projection when viewed from the vertical symmetry plane 3, and a region in which the angle 81 becomes negative exists in the high energy side. Because of this, a bend 111 exists.

Figure 6:
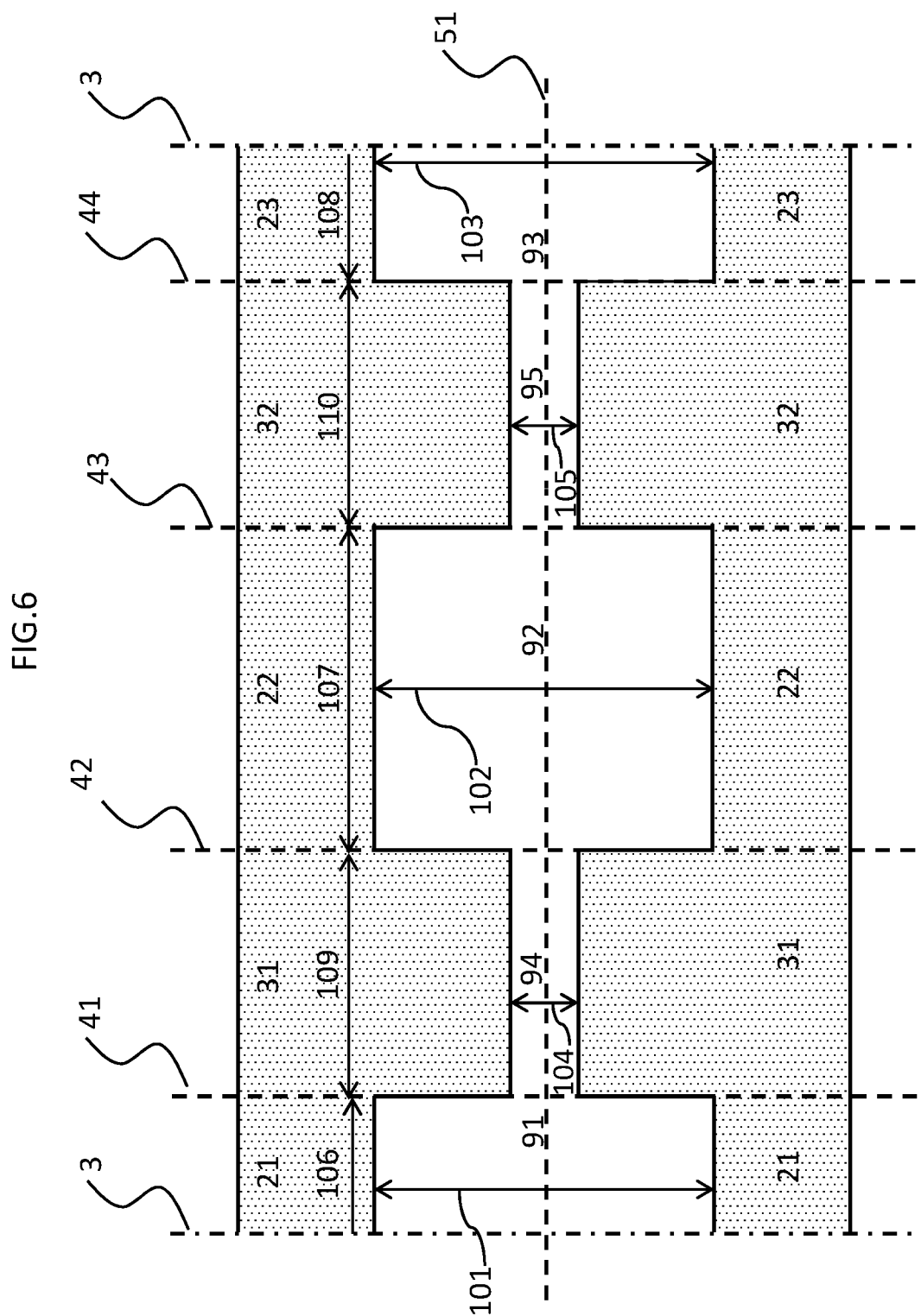
FIG. 6 is a sectional view of a magnetic pole of the sector cyclotron accelerator.

FIG. 6 is a sectional view of a magnetic pole of the magnet apparatus 201 along the beam orbit 51. Because the plurality of depressions and the plurality of projections are designed to be in nearly identical shape, the magnetic pole spacings 101, 102 and 103 are equal to each other and similarly the magnetic pole spacings 104 and 105 are equal to each other. Likewise, magnetic pole widths 106, 107 and 108 are equal to each other, and magnetic pole widths 109 and 110 are also equal to each other.

Figure 7:
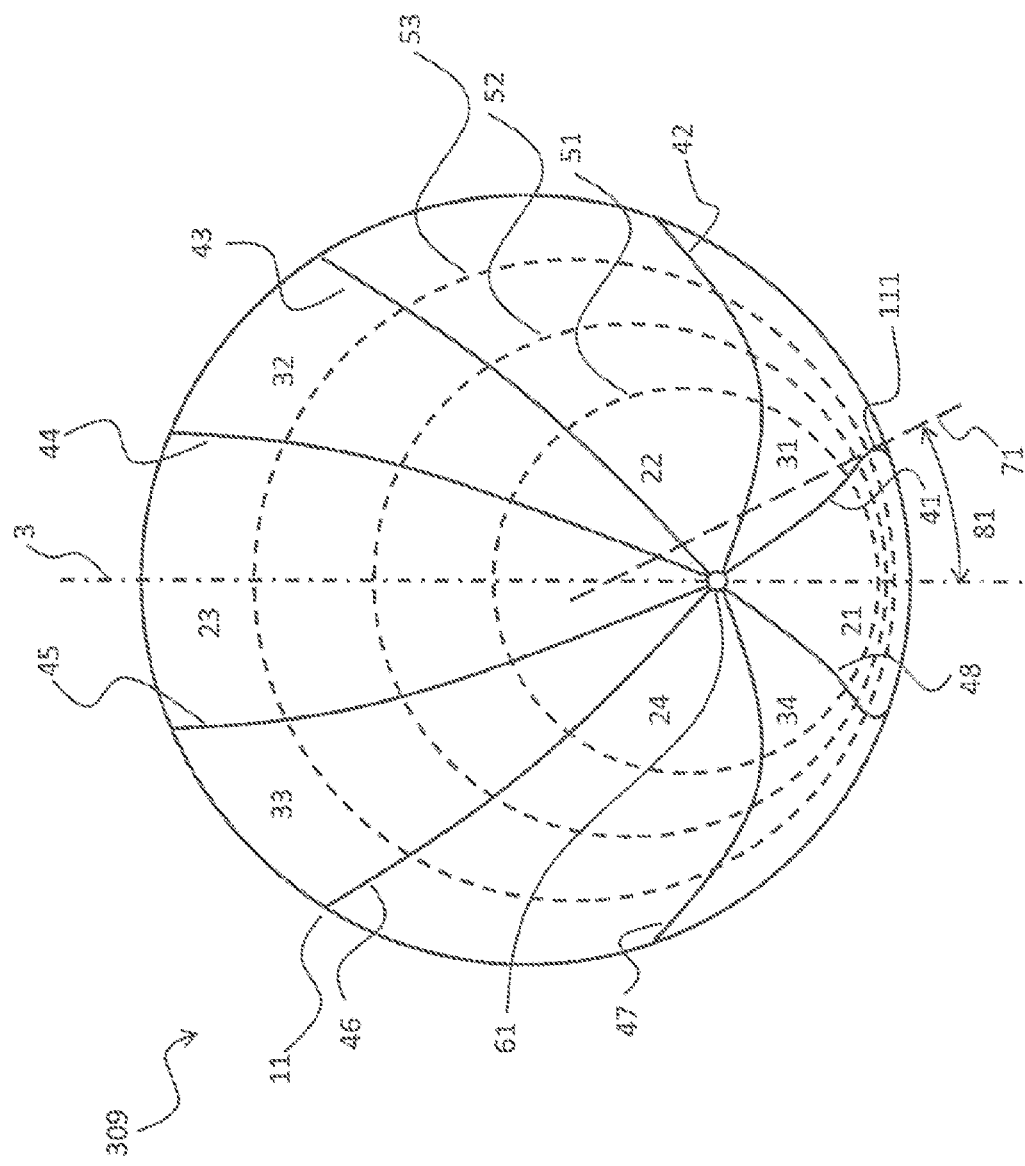
FIG. 7 is a plan view of a magnetic pole surface of a sector cyclotron with eccentric beam orbits.

FIG. 7 is a plan view of a lower magnetic pole 309 obtained by decentering operation to displace the center of each energy orbit in one direction of the vertical symmetry plane 3, for a magnetic pole surface of the magnet apparatus 201. That is, a sectional view of the magnetic pole 309 along the beam orbit 51 matches one in FIG. 6. Since there is a region in FIG. 5 in which the angle 81 becomes negative, there is also a region in FIG. 7 in which the angle 81 becomes negative, and the rate of change of the angle 81 along the direction of the vertical symmetry plane 3 increases, resulting in an increased curvature of the bend 111. The steep boundary bend causes generation of multi-pole components in the magnetic field, and therefore is undesired for beam orbit stability.

To address this, the inventor deformed first the magnetic pole 209 illustrated in FIG. 5 so as to obtain a magnetic pole 409 illustrated in FIG. 8, and then eccentrically displaces each energy beam orbit in one direction of the vertical symmetry plane 3 in order to obtain the lower magnetic pole 9 illustrated in FIG. 3. That is, a sectional view of the lower magnetic pole 409 along the beam orbit 51 matches one in FIG. 4. In this way, by implementing the design without the restriction that the plurality of depressions and the plurality of projections are identical in shape, deformation of the section along the beam orbit such as from FIG. 6 to FIG. 3 was enabled to remove the bend 111 of the boundary surface 41. At this time, for maintaining the isochronal conditions for beams, the magnetic pole 409 is required to have a higher rate of increase of the angle 83 from the void 61 toward the outer periphery 201 than the magnetic pole 209. Then, as illustrated in FIG. 3, when each beam orbit is made eccentric, no bend 111 occurs on the boundary surface 41. And, the boundary surface 43 takes a downward projection shape when viewed from the vertical symmetry plane 3.

As discussed above, in the first embodiment, the boundary surface 41 to the boundary surface 48 are approximately perpendicular to the horizontal symmetry plane 2. Because of this, a large region can be ensured to incorporate equipment into the accelerator magnet, and also the area of the depression 21 containing the vertical symmetry plane 3 is smaller than that of the depression 23. As a result, the turn separations become dense in the valley region 91, whereas the turn separations become sparse in the valley region 93. Additionally, because the boundary surface 41 and the boundary surface 43 are downward projections when viewed from the vertical symmetry plane 3, the stable orbiting of beams is enabled while the isochronicity can be maintained.

Further, because, typically, the beam energy extracted from the cyclotron is a constant value, the energy is adjusted by passing beams through a scatterer called a degrader including a metal plate of aluminum and/or the like. The beam energy can be adjusted by passage through the degrader, but other problems arise, such as an increase in beam size, a decrease in electric current and occurrence of radiation. However, with the accelerator using the magnet apparatus 1 according to the embodiment, the beam energy to be extracted can be varied, and therefore the effect of facilitating inhibiting these problems is provided.

It should be understood that, although the instance of providing the four depressions and the four projections has been described in the embodiment, the present invention is applicable to any case of providing six or more even number of depressions or projections as well.

LIST OF REFERENCE SIGNS 1, 201 . . . Magnet apparatus
2 . . . Horizontal symmetry plane (orbit plane)
3 . . . Vertical symmetry plane (vertical plane)
4 . . . Upper core
5 . . . Lower core
6 . . . Coil
7 . . . Vacuum vessel
8 . . . Upper magnetic pole
9, 209, 309, 409 . . . Lower magnetic pole
10 . . . Magnetic pole surface
11 . . . Outer periphery
21, 22, 23, 24 . . . Depression
31, 32, 33, 34 . . . Projection
41, 42, 43, 44, 45, 46, 47, 48 . . . Boundary surface
51, 52, 53 . . . Beam orbit 61 ... Void (injection point)
71, 72, 73, 74 ... Tangent
81, 82, 83, 84 ... Angle formed between tangent and symmetry plane
91, 92, 93 ... Valley region
94, 95 ... Hill region
101, 102, 103, 104, 105 ... Magnetic pole spacing
106, 107, 108, 109, 110 ... Magnetic width of depression/projection
111 ... Bend

The invention claimed is:

1. An accelerator, having a pair of cores formed in disk shape, a pair of magnetic poles fixed to circular surfaces of the cores, a pair of coils placed around the magnetic poles, and having a space between the pair of the magnetic poles for circulating and accelerating ion beams,
wherein:
the pair of the magnetic poles has a plurality of depression and projection structures arranged along orbits of the ion beams circulating, and the magnetic poles are plane-symmetric with respect to an orbit plane created by the orbits of the circulating ion beams as well as plane-symmetric with respect to a vertical plane perpendicular to the orbit plane,
the pair of the magnetic poles has a depression structure of the plurality of depression and projection structures, in a position intersecting with the vertical plane, and a boundary surface between the depression structure placed in the position intersecting with the vertical plane and a projection structure adjacent to the depression structure has unanimously either a projection shape or a depression shape with respect to the vertical plane,
wherein the core has an ion injection port in a location which is different from a center of an orbit-plane-side surface of the core and which includes the vertical plane,
the plurality of depression and projection structures are each formed in a fan shape having a top at an injection point where the ion injection port is installed, and having an arc along an outer edge of the core,
a depression structure of the depressions intersecting with the vertical plane has a short distance from the injection point to the arc, and a tangent to the boundary surface between the depression structure and a projection structure adjacent to the depression structure forms an acute angle with the vertical plane, and the acute angel monotonically increases as a contact point between the tangent and the boundary surface is moved from the injection point toward the outer edge of the core, and
a depression structure of the depressions intersecting with the vertical plane has a long distance from the injection point to the arc, and a tangent to the boundary surface between the depression structure and a projection structure adjacent to the depression structure forms an acute angle with the vertical plane, and the acute angel monotonically decreases as a contact point between the tangent and the boundary surface is moved from the injection point toward the outer edge of the core.

2. The accelerator according to claim 1, wherein the pair of the magnetic poles has the plurality of depression and projection structures in which spacing amounts between the depression structures placed on the opposite sides of the orbit plane with respect to each other vary among the depression structures located in different positions in an orbit direction of the ion beams.

3. The accelerator according to claim 1, wherein spacing amounts between the projection structures placed on the opposite sides of the orbit plane with respect to each other vary among the projection structures located in different positions in an orbit direction of the ion beams.

4. A particle therapy system comprising the accelerator according to claim 1.

* * * * *